United States Patent [19]

Rayner

[11] Patent Number: 4,563,259

[45] Date of Patent: Jan. 7, 1986

[54] POLYOLEFIN COMPOSITIONS AND ARTICLES STERILIZABLE BY IRRADIATION

[75] Inventor: Martin G. Rayner, Codicote, England

[73] Assignee: Imperial Chemical Industries PLC, Great Britain

[21] Appl. No.: 426,130

[22] Filed: Sep. 28, 1982

[30] Foreign Application Priority Data

Oct. 12, 1981 [GB] United Kingdom ............... 8130687

[51] Int. Cl.$^4$ ..................... C08F 8/00; C08K 5/34
[52] U.S. Cl. ................................. 524/99; 524/102; 524/104; 522/75
[58] Field of Search ............... 524/99, 102; 204/159.2

[56] References Cited

U.S. PATENT DOCUMENTS 4,274,932  6/1981  Williams et al. ................ 204/159.2

FOREIGN PATENT DOCUMENTS

| 7736 | 2/1980 | European Pat. Off. |
| 1390251 | 4/1975 | United Kingdom. |
| 1390252 | 4/1975 | United Kingdom. |
| 1393551 | 5/1975 | United Kingdom. |

OTHER PUBLICATIONS

"The Effects of Sterilising, Processes on Plastics", Bio-Medical Engineering, Sep. 1970, 443–447.
"Radiation Stability of Polypropylene", Radiat. Phys. Chem., 1977, vol. 9, pp. 445–454.
"Instrumentation for High Temperature Analytical GPC", Proceedings of a meeting held at the National Physical Laboratory, Tedidngton, Mar. 1972.
Raff, R. A. V. et al., Crystalline Olefin Polymers—Part II, 338–343 (1964) Interscience Pub. N.Y.
Davis, Thomas E. et al., "Thermal Degradation of Polypropylene" J. Polymer Science, vol. 56, 485–499 (1962).
Nunes, Ronald W. et al., "Influence of Molecular Weight and Molecular Weight Distribution on Mechanical Properties of Polymers"—Polymer Engineering and Science, Mar. 1982, vol. 22, No. 4, 205–228.

*Primary Examiner*—Veronica P. Hoke
*Attorney, Agent, or Firm*—Cushman, Darby & Cushman

[57] ABSTRACT

Polyolefin compositions and articles, especially articles of medical ware, such as polypropylene hypodermic syringes, are made more resistant to the embrittlement which accompanies sterilization by high energy (e.g. gamma) irradiation by the addition to a polyolefin of narrow molecular weight distribution of a heterocyclic hindered amine and, optionally, a liquid modifier.

15 Claims, No Drawings

POLYOLEFIN COMPOSITIONS AND ARTICLES STERILIZABLE BY IRRADIATION

This invention relates to a polyolefin composition, to an article, particularly an article of medical ware, formed from the composition and sterilisable by high energy irradiation, e.g. gamma-irradiation, from a cobalt-60 source, and to a process for the production of such an article.

Polyolefinic articles of medical ware, such as polypropylene syringes have been in use for many years and have been sterilised by gamma-irradiation even though this causes yellow discolouration and/or embrittlement of the syringe despite the presence of non-toxic stabilisers (e.g. British Pat. No. 1 050 802). Plester ("Bio-Medical Engineering" September 1970, pages 443 to 447) disclosed that polypropylene was of only "borderline" suitability for such use and accordingly many attempts have been made to alleviate the problem of discolouration and/or embrittlement on irradiation. Nevertheless, the problem has persisted and was discussed and left unsolved by Williams et al in "Radiation Physics and Chemistry", Volume 9, pages 445 to 454, published in 1977.

European patent publication No. 7736 discloses that the resistance of polyolefins to the discolouration which occurs as a result of gamma-irradiation could be improved by the incorporation therein of one or more specified hindered amines. Typical hindred amines are described in British Pat. Nos. 1 390 251, 1 390 252 and 1 393 551.

A polyolefin has now been devised with improved stability to high energy irradiation.

Accordingly, the present invention provides a composition comprising a substantially crystalline polymer of an aliphatic mono-alpha-olefin the molecule of which contains from 2 to 6 carbon atoms characterised in that the molecular weight distribution ratio of the polymer (Mw/Mn) does not exceed 7.0 and in that the composition comprises from 0.01 to 2.0 (preferably 0.08 to 0.3)% by weight of the polymer of a hindered amine or its salt, N-oxide, N-hydroxide or N-nitroxide wherein the amino nitrogen is contained in a carbon-nitrogen-carbon chain which forms part of a non-aromatic heterocyclic ring and wherein each of the two carbon atoms of the chain is bonded to two lower alkyl groups which may be the same or different each lower alkyl group containing from 1 to 12 carbon atoms or to an alicyclic group containing from 4 to 9 carbon atoms which groups sterically hinder the amine.

The invention also provides an article (eg an article of medical ware) formed from a composition as defined in the immediately preceding paragraph and sterilisable, or sterilised, by exposure to high energy irradiation, such as gamma-irradiation from a cobalt-60 source.

The invention further provides a method of sterilising an article (e.g. an article of medical ware) characterised by forming an article from a composition comprising (a) a substantially crystalline polymer of an aliphatic mono-alpha-olefin the molecule of which contains from 2 to 6 carbon atoms, the molecular weight distribution ratio of the polymer (Mw/Mn) not exceeding 7.0, and (b) from 0.01 to 2.0 (preferably 0.08 to 0.3)% by weight of the polymer of a hindered amine or its salt, N-oxide, N-hydroxide or N-nitroxide wherein the amino nitrogen is contained in a carbon-nitrogen-carbon chain which forms part of a non-aromatic heterocyclic ring and wherein each of the two carbon atoms of the chain is bonded to two lower alkyl groups which may be the same or different, each lower alkyl group containing from 1 to 12 carbon atoms, or to an alicyclic group containing from 4 to 9 carbon atoms, which groups sterically hinder the amine, and exposing the article to a sterilising amount of high energy (e.g. gamma) irradiation.

A hindered amine for use in the compositions of the invention preferably comprises a 5- or 6-membered heterocyclic ring containing the hindered amine nitrogen and optionally another hetero atom preferably nitrogen or oxygen. If the hindered amine is a tertiary amine, the tertiary group may be, for example, an optionally substituted alkyl, aralkyl, alkaryl or alicyclic group containing from 1 to 12 carbon atoms and one or more of the substituents may be hindered amines so that the tertiary group may be used to link a plurality of hindered amines. The hindering groups are preferably lower alkyl groups containing from 1 to 4 carbon atoms and most preferably all four groups are methyl. The most preferred hindered amines comprise 2,2,4,4-tetramethyl piperidine derivatives.

The hindered amine is preferably bonded to a carrier moiety which should have little if any inhibiting effect on the chemical activity of the hindered amine. Reasonably inert carriers include aromatic compounds (for example those based on the benzene, imidazole or triazine rings), saturated hydrocarbon compounds, esters or amides of carboxylic acids, ketones and ether, thioether, sulphinyl or sulphone groups. Preferably, in order to reduce the extractability of the hindered amines from polyolefins, the carriers can be used to link together a plurality of hindered amines and hence the tertiary groups may also be regarded as carriers.

Examples of hindered amines linked by diesters or ketones include:

(a) di-(2,2,6,6-tetramethyl-4-piperidyl)sebacate where the sebacate is the carrier, (b) di-(2,2,6,6-tetramethyl-4-piperidyl) 1-(3,5-ditertiarybutyl-4-hydroxyphenylmethyl)-1,1-pentanedicarboxylate where the pentanedicarboxylate is the carrier, (c) the condensate of succinic acid and N-(2-hydroxyethyl)-2,2,6,6-tetramethyl-4-hydroxypiperidine where both the succinate moiety and the tertiary ethoxy groups combine to form carriers. The condensate preferably contains 6 to 20 hindered amine groups, and (d) 1,4-di-(2,2,6,6-tetramethyl-4-piperidyl)-2,3-butanedione where the butanedione is the carrier.

At least one, and, if desired, a mixture of two or more hindered amines may be included in the compositions of the invention.

The olefin polymer can be, for example, a homopolymer of ethylene (low or high density polyethylene), propylene, butene-1 or 4-methyl-pentene-1, although the term olefin polymer is herein employed to include a copolymer derived from at least one of these monomers and at least one other monomer copolymerisable therewith. Preferred copolymers are copolymers of propylene and either from 7 to 20% (by weight of the copolymer) of ethylene when made by injecting ethylene into the latter stages of an otherwise homopolymerisation of propylene or from 0.5 to 10% of ethylene when made by random copolymerisation. Copolymers of ethylene with up to 30 weight % of vinyl acetate, methyl, ethyl or butyl (including tertiary butyl) acrylates or methacrylates or acrylic or methacrylic acids may also be used. Preferably, the olefin polymer has a melt flow index of from 0.1 to 35, preferably from 5 to 25, g/10 minutes when measured according to British Standard 2782 Part 1/105C of 1970 using a 2.16 kg load at 230° C. in the case of polymers containing a major amount of polymerised propylene and at 190° C. in all other cases. Added rubbers improve impact strength.

Olefin polymers for use in the compositions of the present invention are substantially crystalline, and preferably exhibit a degree of crystallinity, as hereinafter defined, of from 20 to 90%, particularly preferably from 25 to 75%.

The degree of polymer crystallinity is determined by an X-ray technique similar to that described by Natta, Corradini, and Cesari, Rend.Accad.Naz.Lincei 1957, 22,11. By way of example, a typical commercially available propylene homopolymer exhibits a degree of crystallinity, determined by that technique, of the order of 70%.

For comparison of one polymer with another, the breadth of the molecular weight distribution of the polymer is often abbreviated to the ratio Mw/Mn, wherein Mw and Mn are respectively the mean weight and number average molecular weights of the polymer. The minimum molecular weight distribution ratio is 1.0 implying that all the polymer chains are of the same size. The greater the ratio, the broader is the distribution of molecular weight. In accordance with the present invention the molecular weight distribution ratio should not exceed 7.0. Desirably the ratio is from 2 to 6, preferably from 2.5 to 5, and particularly preferably from 2.8 to 3.9.

Molecular weight distribution ratios in accordance with this invention are suitably determined by gel permeation chromatography (GPC), using an apparatus of the kind described by Titterton in an article entitled "Instrumentation for high temperature analytical GPC" delivered at a meeting at the National Physical Laboratory, Teddington, UK, in May 1973 and subsequently printed at pages 83 to 88 of "Industrial Polymers: Characterisation by Molecular Weight" being a compilation of the Proceedings of the aforementioned meeting published by Transcripta Books in June 1973. The operational conditions used are as follows: Silica columns having a nominal porosity range of from 4 to 400 nm packed in such a way as to give an essentially linear calibration of log (M) against elution volume over the elution range of the test samples; 1-methyl naphthalene as solvent stabilised with 1 gram/liter of a suitable antioxidant (such as Topanol OC); an operating temperature of 165° C. (i.e. above the crystalline melting temperature of the polymer sample); a differential refractometer as detector; a sample concentration of 3 grams/liter; a flow rate of 1 ml/minute.

It will be appreciated that GPC data are not absolute but it is possible to standardise against an internationally accepted reference polymer. For olefin polymers, and for the purposes of this invention, the standard reference polymer employed is a linear polyethylene, identification code SRM 1475, available from: U.S.Department of Commerce, National Bureau of Standards, Office of Standard Reference Materials, Washington, D.C. 20234.

To reduce sample to sample variation and experimental error, each experimental value herein quoted for the ratio Mw/Mn is the mean of at least four determinations.

Achievement of the desired narrow molecular weight distribution ratio in the polymers of the invention may be effected by conventional techniques, for example—by appropriate selection of the polymerisation catalyst components and/or reaction conditions in the case of an ethylene polymer or by physical (e.g. thermal) or chemical degradation (e.g. peroxide degradation) in the case of a propylene polymer.

Incorporation of the hindered amine, and other optional additives as hereinafter described, into the composition may be effected by conventional blending techniques at an appropriate stage in the production of the polymer, although it will be appreciated that in the case of a polymer exposed to a degradation technique to achieve the desired molecular weight distribution it may be desirable to incorporate the hindered amine in a subsequent separate blending (e.g. masterbatch) operation to avoid destruction or deterioration of the hindered amine by contact with the degradation medium.

The composition of the invention optionally includes a modifier of the kind described as a "mobilizer" or "mobilizing additive" in U.S. Pat. No. 4,274,932.

The modifier is a low molecular weight non-crystalline substance, which is miscible with the polymeric material and is also compatible therewith, i.e. it does not adversely affect the properties of the polymer. The modifier is a substance which increases the free volume of the polymer and, therefore, also lowers the density of the polymer.

The modifier can be any one of a wide variety of liquids which increase the total free volume of the polymer. The term liquid as used herein includes highly viscous substances commonly referred to as greases. In general, such modifiers have a density of from 0.6 to 1.9 g/cm$^3$, and preferably of from 0.6 to 1.1 g/cm$^3$. The modifier has a low molecular weight, with the average molecular weight, generally being in the order of from 100 to 10,000 grams/mole, and preferably from 100 to 5,000 grams/mole.

Suitable modifiers include: hydrocarbon oils, halogenated hydrocarbon oils, phthalic ester oils, vegetable oils, silicone oils, low molecular weight non-crystalline polymer greases, such as hydrocarbon polymer greases, low molecular weight polyester greases and polyarylether greases. A preferred modifier is a liquid which is not highly viscous, and in particular, a hydrocarbon oil or phthalic ester oil.

The modifier, if employed, is incorporated into the polymer composition in a modifying amount, generally in a range of from 0.1% to 50% and preferably of from 0.1% to 20%, by weight of the composition.

The optionally employed modifier, being of a relatively low molecular weight relative to that of the polymer, will tend to depress the number average molecular weight of the composition. Consequently, prior to assessing the molecular weight distribution ratio of a polymer in a composition containing a modifier, the modifier should first be removed—for example, by solvent extraction.

The composition may also contain stabilising amounts (e.g. 0.01 to 2% by weight of the polymer) of light stabilisers (e.g. benzotriazoles) and/or antioxidants of the kind used in polyolefins, for example, hindered phenols such as n-octadecyl 3-(3,5-ditertiarybutyl-4-hydroxyphenyl)propionate, or organo-phosphonites or organo-phosphites—such as, tris(2,4-di-t-butylphenyl)-phosphite. However, phenolic antioxidants may aggravate discolouration so their use may entail sacrifice of some of the improvement in discolouration. The composition may also contain stabilising amounts of sulphur compounds of the type known to synergise with phenolic antioxidants in polyolefins, for example, long chain (e.g. $C_{10}$ to $C_{22}$) mercaptans and sulphides but the preferred compounds are dialkyl thiodialkanoates especially when the alkyl groups contain from 10 to 22 carbon atoms and the alkanoic acids contain from 2 to 6 carbon atoms. Specific examples are dilauryl and distearyl thiodipropionate. The compositions may contain from 0.01 to 10% (usually 0.1 to 0.5%) by weight of such organic sulphur compounds. Other conventional additives such as pigments or moulding aids may be used.

The compositions of the invention may be used in both medical and non-medical applications, and are of utility in forming a variety of articles—particularly articles of medical ware. Specific articles of sterilisable medical were formed from the compositions of the invention include syringe components (such as barrels, plungers and needle hubs), catheters, cannulae, tissue culture flasks and dishes, forceps, surgical clamps, prosthetic devices, stethoscopes, and components thereof, and also wrappings for such articles. An article of medical ware is an article produced for use (and used) in a medical application (including use in a hospital).

Sterilisation of a composition or article of medical ware in accordance with the invention is effected by exposing the composition or article to a sterilising amount of high energy radiation, for example—electron beam irradiation and particularly gamma irradiation from a cobalt-60 source. A sterilising amount generally comprises from about 0.5 to 10 megarads, a typical dose being in a range of from about 1.0 to 5.0 megarads and usually from about 1.5 to 3.5 megarads.

The invention is illustrated by reference to the following examples.

EXAMPLES 1 TO 11

Using a high speed powder mixer, powdered propylene homopolymer was mixed with various amounts of various powdered additives to yield the respective formulations specified in the accompanying Table 1. Each powder formulation was heated to a temperature of 260° C. to melt the polymer and the melt was converted to granules. Type I tensile bars (as specified in ASTM D 638) of overall width 19 mm, overall length 213 mm and thickness 1.6 mm, were formed from each granular formulation by injection moulding.

Sample bars from each formulation were retained as controls and the rest were irradiated at 2.5 Mrad using a cobalt-60 source. The control and irradiated bars were divided into eight groups.

The bars of the first group were placed in an air-circulating oven maintained at a temperature of 150° C. and were visually inspected each day for the appearance of surface cracking which is indicative of embrittlement. The number of days (24 hours) elapsing before the onset of embrittlement in a bar is recorded as the oven life of the bar at the specified oven temperature.

The bars of the second group were similarly assessed for embrittlement save that the bars were kept in an air-circulating oven maintained at a temperature of 135° C. until surface cracking became evident.

The bars of the third to eighth groups were respectively stored under the following conditions:

Group 3: 1 calender month at ambient temperature (25° C.),

Group 4: 5 calender months at ambient temperature (25° C.),

Group 5: 8.5 calendar months at ambient temperature (25° C.),

Group 6: 24 days (of 24 hours) in an air-circulating oven maintained at a temperature of 70° C., Group 7: 48 days (of 24 hours) in an air-circulating oven maintained at a temperature of 60° C.

Group 8: 43 hours in an air-circulating oven maintained at a temperature of 110° C.

Thereafter, the Percentage Elongation at Break of the stored bars was assessed by the standard method of ASTM D638, save that the increase in jaw separation at break was recorded relative to a nominal gauge length of 50 mm. The quoted percentage values are therefore relative rather than absolute. Testing of the bars of the third to seventh groups was effected at Speed C, ie 50 mm/minute; those of the eighth group were tested at a speed of 25 mm/minute.

Results are recorded in the accompanying Table 2.

TABLE 1

| | | Additive Formulation (% by weight of polymer) | | | | | |
|---|---|---|---|---|---|---|---|
| Ex. | Polymer type* | Calcium stearate | Anti-oxidant** | Thioester | Hindered amine derivative | Modifier | Mw/MN |
| 1 | A | 0.2 | 0.1 | 0.25$^a$ | | | 7.6 |
| 2 | A | 0.2 | 0.1 | | | | |
| 3 | B | 0.2 | | | | | |
| 4 | B | 0.2 | | | | 5.3$^d$ | |
| 5 | B | 0.2 | 0.1 | | | | 3.4 |
| 6 | B | 0.2 | 0.1 | | 0.2$^b$ | | 3.4 |
| 7 | B | 0.2 | | | 0.2$^b$ | | 3.5 |
| 8 | B | 0.2 | | | 0.2$^b$ | 5.3$^d$ | 3.9$^e$ |
| 9 | B | 0.2 | | | 0.1$^c$ | | |
| 10 | C | | 0.1 | | 0.2$^b$ | | 2.8 |
| 11 | D | — | | | | | 2.9 |

*A = Propylene homopolymer - broad molecular weight distribution.
B = Propylene homopolymer - narrow molecular weight distribution.
C = Propylene-ethylene (<5 wt % E) random copolymer - narrow molecular weight distribution.
D = Standard reference polymer - SRM1475.
**Conventional antioxidant for olefin polymer.
$^a$ - Dilauryl thiodipropionate.
$^b$ - Condensate of succinic acid and N—(2-hydroxyethyl)-2,2,6,6-tetramethyl-4-hydroxypiperidine.
$^c$ - Di-(2,2,6,6-tetramethyl-4-piperidyl)sebacate.
$^d$ - 'Kaydol' white mineral oil - 'Kaydol' is a Trademark of Witco Chemical Corporation.
$^e$ - After solvent extraction of the mineral oil.

TABLE 2

| Ex. | Irradiation (Mrad) | Oven Life (days) at 150° C. | Oven Life (days) at 135° C. | Elongation at Break (%), after storage for: 1 month at 25° C. | 5 months at 25° C. | 8.5 months at 25° C. | 24 days at 70° C. | 48 days at 60° C. | 43 hours at 110° C. |
|---|---|---|---|---|---|---|---|---|---|
| 1 | 0 |  |  | 40 |  |  | 30 |  | 40 |
|  | 2.5 |  |  | 30 |  |  | 30 |  | 30 |
| 2 | 0 | 1 | 4 | 50 | 30 | 20 | 50 | 40 | 20 |
|  | 2.5 | 1 | 1 | 30 |  |  | 20 | 20 |  |
| 3 | 0 |  |  | >900 |  |  |  |  | >500 |
|  | 2.5 |  |  | >900 |  |  |  |  | 50 |
| 4 | 0 |  |  | >900 |  |  |  |  | >500 |
|  | 2.5 |  |  | >900 |  |  |  |  | 30 |
| 5 | 0 | 1 | 4 | >900 | 890 | 380 | 180 | 270 |  |
|  | 2.5 | 1 | 1 | >900 |  |  | 30 | 30 |  |
| 6 | 0 |  |  | >900 | >900 | >900 | 140 | 180 |  |
|  | 2.5 |  |  | >900 |  |  | 120 | 160 |  |
| 7 | 0 | 6 | 38 | >900 | >900 | >900 | 240 | 540 | >500 |
|  | 2.5 | 6 | 28 | >900 |  |  | 160 | 470 | >500 |
| 8 | 0 |  |  |  | >900 | >900 | 330 | 260 |  |
|  | 2.5 |  |  |  |  |  | 140 | 410 |  |
| 9 | 0 |  |  | >900 |  |  |  |  | >500 |
|  | 2.5 |  |  | >900 |  |  |  |  | >500 |
| 10 | 0 |  |  |  |  |  |  | >900 | >500 |
|  | 2.5 |  |  |  |  |  |  | >900 | >500 |

The absence of an entry in the tables means that the additive in question was not present in the formulation or that the particular parameter was not measured.

Examples 1 to 5, which are comparative, and not according to the invention, demonstrate the poor stability to irradiation of propylene polymers of both broad and narrow molecular weight distribution even when additioned with conventional antioxidants and synergists. The remaining examples illustrate the surprising improvement in stability conferred by the combination of a narrow molecular weight distribution polymer and a hindered amine derivative—with the optional addition of a modifier, according to the invention. The samples according to the invention resist embrittlement and retain a degree of ductility (as measured) after irradiation and storage under the specified conditions.

I claim:

1. A polyolefin composition comprising a substantially crystalline polymer of an aliphatic mono-alpha-olefin the molecule of which contains from 2 to 6 carbon atoms wherein the molecular weight distribution ratio of the polymer (Mw/Mn) does not exceed 7.0 and from 0.01 to 2.0% by weight of a polymer of a hindered amine or its salt, N-oxide, N-hydroxide or N-nitroxide wherein the amino nitrogen is contained in a carbon-nitrogen-carbon chain which forms part of a non-aromatic heterocyclic ring and wherein each of the two carbon atoms of the chain is bonded to two lower alkyl groups which may be the same or different, each lower alkyl group containing from 1 to 12 carbon atoms, or to an alicyclic group containing from 4 to 9 carbon atoms, which groups sterically hinder the amine, and wherein the composition is sterilized by exposure to a sterilizing amount of high energy irradiation.

2. A polyolefin composition according to claim 1 wherein the composition additionally comprises a modifying amount of a modifier, said modifier being a low molecular weight non-crystalline material which is miscible and compatible with the polymer and which increases the free volume of the polymer.

3. A composition according to claim 1 wherein the hindered amine comprises a 6-membered heterocyclic ring.

4. A composition according to claim 1 wherein the hindered amine is carried by a carrier selected from the group consisting of a dicarboxylate, a triazine ring and a diketone.

5. A composition according to claim 2 wherein the modifier is selected from the group consisting of hydrocarbon oils, halogenated hydrocarbon oils, phthalic esters, polymer greases, vegetable oils and silicone oils.

6. An article formed from a composition according to claim 1.

7. An article according to claim 6 wherein the article is a component for a hypodermic syringe.

8. An article according to claim 6 wherein the article is an article of medical ware.

9. An article according to claim 6 wherein the article is an article of medical ware and wherein the high energy irradiation is high energy gamma irradiation.

10. A method of sterilizing an article by forming an article from a composition comprising (a) a substantially crystalline polymer of an aliphatic mono-alpha-olefin the molecule of which contains from 2 to 6 carbon atoms, the molecular weight distribution ratio of the polymer (Mw/Mn) not exceeding 7.0, and (b) from 0.01 to 2.0% by weight of the polymer of a hindered amine or its salt, N-oxide, N-hydroxide or N-nitroxide wherein the amino nitrogen is contained in a carbon-nitrogen-carbon chain which forms part of a non-aromatic heterocyclic ring and wherein each of the two carbon atoms of the chain is bonded to two lower alkyl groups which may be the same or different, each lower alkyl group containing from 1 to 12 carbon atoms, or to an alicyclic group containing from 4 to 9 carbon atoms, which groups sterically hinder the amine, and exposing the article to a sterilizing amount of high energy irradiation.

11. A method according to claim 10 wherein the composition additionally comprises a modifier, said modifier being a low molecular weight non-crystalline material which is miscible and compatible with the polymer and which increases the free volume of the polymer.

12. A method as in claim 10 wherein the article is an article of medical ware.

13. The method as in claim 10 wherein the hindered amine or salt is present in an amount between 0.08 to 0.3% by weight of the polymer.

14. The method as in claim 12 or 13 wherein the high energy irradiation is high energy gamma irradiation.

15. An article sterilized according to the method of claim 10.

* * * * *